US010617621B2

(12) United States Patent
Cawley et al.

(10) Patent No.: US 10,617,621 B2
(45) Date of Patent: Apr. 14, 2020

(54) ANTIMICROBIAL COMPOSITION

(71) Applicant: Conopco, Inc., Englewood Cliffs, NJ (US)

(72) Inventors: Andrew Cawley, Liverpool (GB); Michael John Hoptroff, Birkenhead (GB); Mingming Pu, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/325,362

(22) PCT Filed: Aug. 10, 2017

(86) PCT No.: PCT/EP2017/070304
§ 371 (c)(1),
(2) Date: Feb. 13, 2019

(87) PCT Pub. No.: WO2018/033466
PCT Pub. Date: Feb. 22, 2018

(65) Prior Publication Data
US 2019/0201312 A1 Jul. 4, 2019

(30) Foreign Application Priority Data

Aug. 19, 2016 (WO) ............... PCT/CN2016/000470
Sep. 22, 2016 (EP) ................................. 16190042

(51) Int. Cl.
*A61K 8/49* (2006.01)
*A61Q 5/02* (2006.01)
*A61Q 5/12* (2006.01)
*A61Q 17/00* (2006.01)

(52) U.S. Cl.
CPC ............ *A61K 8/4933* (2013.01); *A61K 8/494* (2013.01); *A61Q 5/02* (2013.01); *A61Q 5/12* (2013.01); *A61Q 17/005* (2013.01); *A61K 2800/592* (2013.01)

(58) Field of Classification Search
None
See application file for complete search history.

(56) References Cited

U.S. PATENT DOCUMENTS

| | | |
|---|---|---|
| 4,185,106 A | 1/1980 | Dittmar et al. |
| 2002/0028754 A1 | 3/2002 | Jonansen et al. |
| 2003/0224028 A1 | 12/2003 | Galey |
| 2003/0232063 A1 | 12/2003 | Galey et al. |
| 2004/0087668 A1 | 5/2004 | Schmucker-Castner et al. |
| 2005/0277694 A1 | 12/2005 | Prieto et al. |
| 2007/0202069 A1 | 8/2007 | Tamareselvy et al. |
| 2009/0197791 A1 | 8/2009 | Balastre et al. |
| 2010/0143515 A1 | 6/2010 | Faller et al. |
| 2013/0079353 A1 | 3/2013 | Gulow |
| 2013/0171080 A1 | 7/2013 | Sarkar et al. |
| 2014/0335029 A1 | 11/2014 | Rudolph et al. |
| 2014/0364595 A1 | 12/2014 | Bapat et al. |
| 2015/0118165 A1 | 4/2015 | Rudolph et al. |
| 2015/0118172 A1 | 4/2015 | Rudolph et al. |
| 2016/0015031 A1 | 1/2016 | Pesaro et al. |

FOREIGN PATENT DOCUMENTS

| | | |
|---|---|---|
| CN | 102743363 | 4/2011 |
| CN | 104225603 | 12/2014 |
| CN | 102218048 | 1/2015 |
| EP | W00139735 | 6/2001 |
| EP | 1961410 | 8/2008 |
| GB | 2357968 | 7/2001 |
| KR | 20140052576 | 10/2012 |
| WO | WO9729733 | 8/1997 |
| WO | WO00040207 | 7/2000 |
| WO | WO2004006876 | 1/2004 |
| WO | WO2004035012 | 4/2004 |
| WO | WO2013010706 | 10/2013 |
| WO | WO2014131191 | 9/2014 |
| WO | WO2014191258 | 12/2014 |
| WO | WO2015100122 | 7/2015 |
| WO | WO2015198338 | 12/2015 |
| WO | WO2016012797 | 1/2016 |
| WO | WO2016012973 | 1/2016 |

OTHER PUBLICATIONS

Hall et al.; The fractional inhibitory concentration (FIC) index as a measure of synergy; Journal of Antimicrobial Chemotherapy; Jan. 1, 1983; pp. 427-433 XP-008091249; v. 11 No. 5; United Kingdom.
Search Report and Written Opinion in PCTEP2017068105; dated Oct. 30, 2017.
Writtten Opinion in PCTEP2017070304; dated Sep. 29, 2017.
Lee et al.; Mapping the Cellular Response to Small Molecules Using Chemogenomic Fitness Signatures; Science; Apr. 11, 2014; pp. 344, No. 6180; vol. 344, No. 6180; United States of America.
Search Report & Written Opinion in EP16192161; dated Jan. 10, 2017.
Search Report & Written Opinion in EP16190042; dated Nov. 8, 2016.
Shampoo; Minteal GNPD 2006—XP-002763449; 2010; XP-002763449 http://www.gnpd.com;.
Search Report & Written Opinion in EP16190028; dated Nov. 9, 2016.
Anti-Dandruff Shampoo; Mintel 2006—XP-002763447; 2006; XP-002763447; http://www.gnpd.com; United States of America.
Search Report and Written Opinion in PCTEP2017070316; dated Sep. 29, 2017.

(Continued)

*Primary Examiner* — Nannette Holloman
(74) *Attorney, Agent, or Firm* — Foley & Lardner LLP

(57) ABSTRACT

This invention relates to an antimicrobial composition, especially one which provides synergistic anti-dandruff efficacy. This is achieved through a judicious combination of anti-dandruff agent zinc pyrithione and a piperazine compound of specific type. These compositions can be delivered through very many different types of personal care products e.g. shampoo or conditioner.

15 Claims, No Drawings

(56) References Cited

OTHER PUBLICATIONS

Magnolia Shampoo; Mintel GNPD 2006—XP-002763448; 2006; XP-002763448 http://www.gnpd.com, United States of America.
Deangelis et al.; Three Etiologic Facets of Dandruff and Seborrheic Dermatitis: Malassezia Fungi, Sebaceous Lipids, and Individula Sensitivity; Journal of Investigative Dermatology Symposium Proceedings ; 2005; pp. 295-297; 10(3).

ANTIMICROBIAL COMPOSITION

CROSS REFERENCE TO RELATED APPLICATIONS

The present application is a U.S. National Phase Application under 35 U.S.C. § 371 of International Application No. PCT/EP2017/070304 filed on Aug. 10, 2017, which claims priority to European patent application No. 16190042.8 filed on Sep. 22, 2016 and International Application No. PCT/CN2016/000470 filed on Aug. 19, 2016, the contents of which are incorporated herein in their entireties.

FIELD OF THE INVENTION

This invention relates to an antimicrobial composition. The invention more particularly relates to a personal care composition e.g those for hair, body and face wash which provides anti-microbial efficacy. It more particularly relates to a cleansing composition for hair and scalp comprising actives that interact to provide synergistic antimicrobial efficacy for anti-dandruff benefits.

BACKGROUND OF THE INVENTION

The invention relates to an anti-microbial composition useful for cleaning of any body part but especially suitable for hair and scalp. Hair care compositions generally provide cleansing or conditioning benefits or a combination of the two. Such compositions typically comprise one or more cleansing surfactants which generally aid in cleaning the hair and/or the scalp free of undesirable soil, particles, and fatty matter.

Additionally, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff are certain members of the *Malassezia* yeasts. To combat these, anti-dandruff products have been developed in the form of hair cleansing shampoos. An example of a known anti-dandruff shampoo comprises sodium lauryl ether sulfate (an ethoxylated anionic surfactant) in combination with an anti-dandruff agent. Typical anti-dandruff agents used in hair care are metal pyrithione e.g zinc pyrithione (ZPTO), octopirox (piroctone olamine), azole antimicrobials (e.g. climbazole), selenium sulfide and combinations thereof.

While the problem of dandruff is mitigated to a large extent through use of the above actives in such shampoos, there is a need for enhancing the efficacy of these actives. The present inventors have found through a combination of exploring very many possible mechanisms by which the efficacy of one of the above actives (zinc pyrithione) can be enhanced together with extensive experiments on possible enhancer candidates that a certain compounds of the piperazine class display such enhancing properties. The synergistic antimicrobial combination of this invention can also be formulated into products for skin cleansing e.g. body and face care.

Piperazines are a very large family of compounds which have been reported for very many different uses including as sunscreen agents and has been reported to be used in skin care compositions.

WO97/29733 (Neutrogena) discloses a composition comprising a fungal ergosterol biosynthesis antifungal (preferably an azole or an allylamine) and a pyrithione salt.

A. Y. LEE ET AL: "Mapping the Cellular Response to Small Molecules Using Chemogenomic Fitness Signatures", SCIENCE, vol. 344, no. 6180, 11 Apr. 2014 (2014 Apr. 11), pages 208-211 ("the science paper") discloses a study on mapping the cellular response to small molecules with a yeast-genomic tool in loss of function assays. This paper discloses the molecules 13, 17, 22 and 26, (which are similar to the compounds claimed in the present invention) to target the ergosterol biosynthesis and its function in the membrane.

The above two publications disclose compounds which singly or in combination are reported to knock down ergosterol biosynthesis and function in yeast.

Thus, there is no report of the actives of the present invention in combination with metal pyrithione nor is there any indication that they can be combined to provide synergistic anti-microbial activity.

It is thus an object of the present invention to provide for a personal care composition that exhibits synergistic antimicrobial activity as compared to the individual components.

SUMMARY OF THE INVENTION

According to the first aspect of the present invention there is a synergistic antimicrobial composition comprising
(i) A polyvalent metal salt of pyrithione; and
(ii) A piperazine compound selected from 1-(2-fluorobenzoyl)-4-(4-phenylcylcohexyl) piperazine, 1-(3-chlorobenzyl)-4-(4-ethylbenzyl)piperazine oxalate, 1-(4-fluorophenyl)-4-isobutyrylpiperazine, 1-isobutyryl-4-phenylpiperazine, or 1-(4-ethylbenzyl)-4-(4-methylcyclohexyl)piperazine oxalate.

The second aspect of the present invention relates to a method of inhibiting the growth of *Malassezia furfur* comprising the step of applying a composition as claimed in the first aspect, on the scalp of an individual.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. In other words, in specifying any ranges of values, any particular upper value can be associated with any particular lower value.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By 'an antimicrobial composition' as used herein, is meant to include a composition for topical application to skin, hair and/or scalp of mammals, especially humans. Such a composition is generally applied on to the desired topical surface of the body for a period of time from a few seconds to up to 24 hours. When the period of time of application is low say of the order of a few seconds to a few minutes after which the composition is rinsed off with water or wiped away, such a composition is known as a cleansing composition or a wash-off composition. When the composition is applied for longer period of time say from several minutes to up to 24 hours and washed off usually during the process of normal personal cleaning, such a composition is known as a leave-on composition. The composition as per the present invention may be of the wash-off or of the leave-on type. Of the two, it is preferably of the wash-off type. It includes any product applied to a human body for also improving appearance, cleansing, odor control or general aesthetics. The composition of the present invention can be in the form of a liquid, lotion, cream, foam, scrub, gel, or bar. Non-limiting examples of such compositions include wash-off shampoos, conditioners, shower gels, hand wash liquids or gels or bars. The composition of the present invention is most preferably a shampoo or a conditioner. It is most preferably used for preventing or alleviating the symptoms of dandruff on the scalp and/or hair.

The present invention more particularly relates to an antimicrobial cleansing composition. A preferred aspect is an anti-dandruff hair care composition. It comprises synergistic anti-fungal action of the polyvalent metal salt of pyrithione e.g. zinc pyrithione with the piperazine compound claimed in the present invention.

The preferred polyvalent metal salt of pyrithione is zinc pyrithione (ZPTO) which is shorthand for zinc 1-hydroxy-2-pyridinethione.

The polyvalent metal salt of pyrithione is represented by the following general formula:

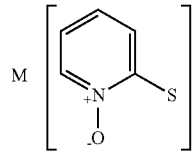

In the case of zinc pyrithione, M is the metal cation zinc.

Zinc pyrithione is preferably present in 0.1 to 5.0%, more preferably from 0.1 to 2.0% based on weight of the composition. ZPTO is a particulate material. While the particle size is not critical to achieve the benefits of the present invention, the particle size of ZPTO is preferably from 0.25 to 8 micrometer, more preferably from 0.5 to 8.0 micrometer, and further more preferably from 1.0 to 7.5 micrometer. ZPTO is commercially available from Kolon Life Science Inc., Sino Lion (USA) Ltd, Lonza, and other suppliers.

The piperazine compound is preferably chosen 1-(2-fluorobenzoyl)-4-(4-phenyl cylcohexyl) piperazine, 1-(3-chlorobenzyl)-4-(4-ethylbenzyl)piperazine oxalate, 1-(4-fluorophenyl)-4-isobutyrylpiperazine, 1-isobutyryl-4-phenylpiperazine, or 1-(4-ethylbenzyl)-4-(4-methylcyclohexyl)piperazine oxalate which have the chemical structures given below.

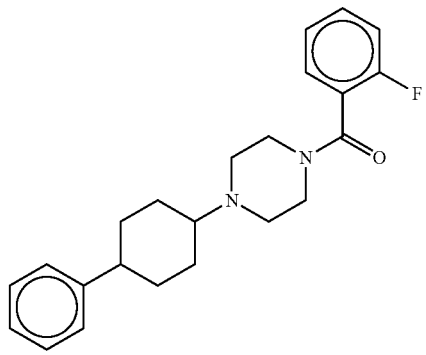

1-(2-fluorobenzoyl)-4-(4-phenyl cylcohexyl)piperazine

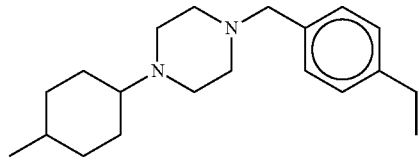

1-(4-ethylbenzyl)-4-(4-methylcyclohexyl)piperazine oxalate

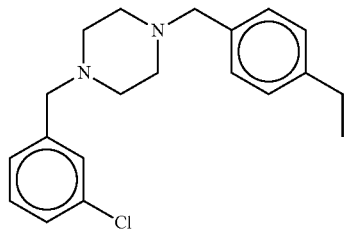

1-(3-chlorobenzyl)-4-(4-ethylbenzyl)piperazine oxalate

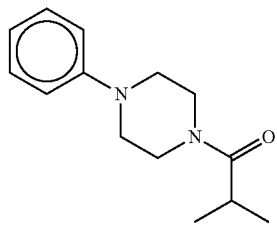

1-isobutyryl-4-phenylpiperazine

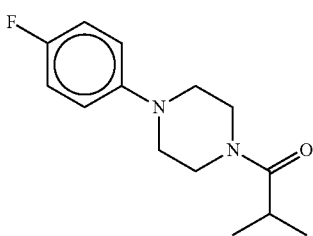

1-(4-fluorophenyl)-4-isobutyrylpiperazine

The piperazine compounds used in the present invention have been synthetically prepared and commercially available from Chem Bridge Corporation, CA, USA.

The piperazine compound is preferably present in 0.1 to 10%, more preferably from 0.1 to 5%, further more preferably 0.2 to 3.0% based on the total weight of the composition. According to a preferred aspect of the present invention the piperazine compound is 1-(2-fluorobenzoyl)-4-(4-phenyl cylcohexyl) piperazine or 1-(3-chlorobenzyl)-4-(4-ethylbenzyl) piperazine oxalate.

Without wishing to be bound by theory, the inventors believe that the anti-microbial efficacy of ZPTO is enhanced by the piperazine compounds through perturbation of microbial membrane integrity.

The present inventors have found that compounds with the same yeast chemogenomic response on ergosterol as ketoconazole do not necessarily show synergistic efficacy in combination with zinc pyrithione. For example, the present inventors have tested various other compounds (as below with the same function as documented in Table 2 of the Science paper) in combination with zinc pyrithione.

5-chloro-2-(4-isobutyryl-1-piperazinyl)aniline

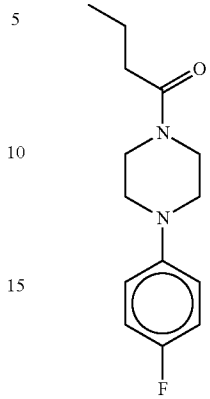

1-butyryl-4-(4-fluorophenyl)piperazine

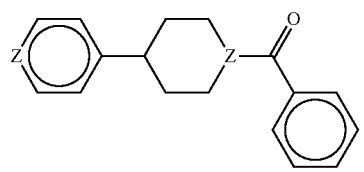

4-(1-benzoyl-4-piperidinyl)pyridine

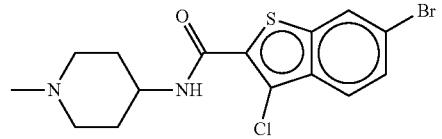

6-bromo-3-chloro-N-(1-methyl-4-piperidinyl)-1-benzothiophene-2-carboxamide

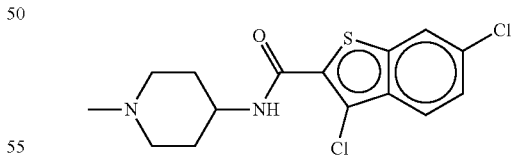

3,6-dichloro-N-(1-methyl-4-piperidinyl)-1-benzothiophene-2-carboxamide

None of the above compounds show synergy with zinc pyrithione for anti-*Malassezia* efficacy. Hence, simply replacing ketoconazole with other ergosterol inhibitors does not necessarily translate to synergistic anti-*Malassezia* efficacy.

The present inventors thus demonstrate that piperazine compounds claimed in the present invention in combination

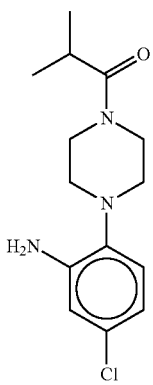

1-acetyl-4-(2,3-dimethylphenyl)piperazine with zinc pyrithione is synergistic, and this behavior is not seen with many other compounds which are replacement of the azole compounds disclosed in WO97/29733.

The composition of the invention preferably comprises a cosmetically acceptable carrier. According to one aspect the cosmetically acceptable carrier comprises water. According to another preferred aspect, the carrier additionally comprises a surfactant.

According to a further preferred aspect of the present invention, the composition is either a shampoo or a hair conditioner.

Shampoo

As per an especially preferred aspect of the invention, the composition is a shampoo. The composition of the invention especially shampoos are formulated with an anionic surfactant e.g. an alkyl sulphate and/or ethoxylated alkyl sulfate surfactant. These anionic surfactants are preferably present at a level of from 1 to 20%, preferably 2 to 16%, further more preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium.

Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES). SLES having an average degree of ethoxylation of from 0.5 to 3, preferably 1 to 3 is especially preferred.

Shampoo compositions according to the invention may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

A composition of the invention preferably additionally comprises an amphoteric surfactant preferably a betaine surfactant preferably an alkyl amidopropyl betaine surfactant for example cocamidopropyl betaine. In a preferred embodiment, the composition comprises from 0.1 to 10 wt. %, preferably from 0.5 to 8 wt. %, more preferably from 1 to 5 wt. % of a betaine surfactant To enhance deposition of actives from compositions of the invention especially shampoos, cationic polymers are generally included therein. In the present invention too, it is preferred that the composition additionally includes 0.01 to 2.0% of a cationic polymer. The cationic polymer is preferably guar hydroxypropyl trimonium chloride. Guar polymer predominantly contains galactomannan polymer chains. This polymer is available at various molecular weights and degree of cationic substitutions depending on how much the guar has been hydrolysed and cationised. The cationic polymer is preferably present in 0.04 to 0.5%, more preferably 0.08 to 0.25% by weight of the composition.

The pH of the composition is preferably equal to or higher than 4.0, more preferably in the range of 5.0 to 7.0.

The composition as per the invention especially for antidandruff shampoos preferably additionally comprises a zinc compound. The presence of additional zinc compound in the composition is believed to improve the antidandruff efficacy of the metal salt of pyrithione. Suitable zinc compounds are zinc oxide, zinc citrate, zinc malonate, zinc carbonate or combinations thereof. The zinc compound is preferably present in 0.1 to 3%, more preferably 0.1 to 1.5% by weight of the composition.

Shampoo composition as per the invention preferably additionally comprises a conazole fungicide. Preferably the conazole fungicide is selected form ketoconazole, climbazole or mixtures thereof. The azole fungicide is preferably included in 0.01 to 2%, more preferably 0.025 to 0.75% by weight of the composition. The presence of a conazole fungicide is believed to improve the deposition of zinc pyrithione.

The composition preferably additionally comprises a vitamin B3 compound. The preferred vitamin B3 compound is niacinamide.

Niacinamide has the structure as given below

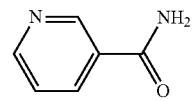

Niacinamide is known for secretion of AMPs from keratinocytes. The AMPs thus secreted provides for improving the immunity of the external surface of the body e.g. on the scalp. Thus with the use of niacinamide in the composition of the invention the anti-dandruff efficacy is expected to be enhanced not just through anti-fungal activity of the composition of the invention but by providing a boost to the scalp's own protection shield against germs, through use of niacinamide. It is expected that this combination could provide further long-lasting protection e.g. up to 24 hours of protection against germs.

Niacinamide is preferably present in 0.1 to 5%, more preferably 0.5 to 5%, further more preferably 0.5 to 3%, and optimally 1.0 to 3.0% by weight of the composition.

Suspending Agent

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent, if included, will generally be present in a shampoo composition of the invention at levels of from 0.1 to 10%, preferably from 0.5 to 6%, more preferably from 0.5 to 4% by total weight of suspending agent based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

The composition of the invention is preferably aqueous based. It preferably comprises high amounts of water preferably from 70 to 95% by weight of the composition.

Hair Conditioner

When conditioning benefits are to be delivered through the composition of the invention the composition is called a hair conditioner. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Amounts of the silicone in compositions where present may range from about 0.1 to about 10 wt. %, preferably from about 0.1 to about 8 wt. %, more preferably from about 0.3 to about 5 wt. % by weight of the hair care compositions.

The pH of the composition is preferably equal to or higher than 4.0, more preferably in the range of 5.0 to 7.0.

The hair conditioning composition usually comprises conditioning surfactants selected from cationic surfactants, used singly or in admixture. Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1% to 5%, preferably 0.5 to 2.5% by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.5 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, more preferably from 1:1.5 to 1:8, optimally from 1:2 to 1:5.

Skin Cleansing

The composition of the invention may be used for skin care e.g. body or face wash. The antimicrobial composition may further comprise a surfactant. The preferred surfactants are nonionic surfactants, such as $C_8$-$C_{22}$, preferably $C_8$-$C_{16}$ fatty alcohol ethoxylates, comprising between 1 and 8 ethylene oxide groups when the product is in the liquid form. The surfactants are preferably selected from primary alkyl sulphate, secondary alkyl sulphonates, alkyl benzene sulphonates, or ethoxylated alkyl sulphates. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16.

Thus, in a highly preferred aspect, the antimicrobial compositions include the surfactant selected from the group of anionic surfactant, fatty acid amide, alkyl sulphate, linear alkyl benzene sulphonate, and combinations thereof.

When the surfactants are present, the antimicrobial composition preferably comprises 1 to 90% surfactant by weight of the composition When surfactant is used, a particularly preferred surfactant is soap. Soap is a suitable surfactant for personal washing applications of the antimicrobial composition of the invention. The soap is preferably $C_8$-$C_{24}$ soap, more preferably $C_{10}$-$C_{20}$ soap and most preferably $C_{12}$-$C_{18}$ soap. The cation of the soap can be alkali metal, alkaline earth metal or ammonium. Preferably, the cation of the soap is selected from sodium, potassium or ammonium. More preferably the cation of the soap is sodium or potassium.

A typical fatty acid blend consisted of 5 to 30% coconut fatty acids and 70 to 95% fatty acids by weight of soap. Fatty acids derived from other suitable oils/fats such as groundnut, soybean, tallow, palm, palm kernel, etc. may also be used in other desired proportions.

When present, the soap, of the present is preferably present in an amount of 1 to 90%, preferably from 10 to 85%, more preferably 25 to 75% by weight of the composition.

Preferred compositions may include other known ingredients such as perfumes, pigments, preservatives, emollients, sunscreens, emulsifiers, gelling agents and thickening agents. Choice of these ingredients will largely depend on the format of the composition.

Water is a preferred carrier. When water is present, it is preferably present in at least 1%, more preferably at least 2%, further more preferably at least 5% by weight of the composition. When water is the carrier, a preferred liquid composition comprises 10 to 99.8% by weight water. The liquid antimicrobial composition is useful as a skin antiseptic liquid, for skin cleansing, in particular for hand wash or a face wash. When water is the carrier, a preferred solid composition comprises 5 to 30% by weight water.

The solid antimicrobial composition is preferably in form of a shaped solid, more preferably a bar. The solid antimicrobial composition is particularly useful for skin cleansing in particular for hand wash or a face wash.

According to another aspect, inorganic particulate material is also a suitable carrier. When inorganic particulate material is the carrier, the antimicrobial composition is in a solid form. Preferably the inorganic particulate material is talc. When the inorganic particulate material is talc, the solid antimicrobial composition is particularly useful as a talcum powder for application on face or body.

According to a further aspect, a solvent is a preferred carrier. Although any solvent can be used, alcohol is a preferred solvent. Short chain alcohols, in particular ethanol and propanol, are particularly preferred as carrier for an antimicrobial wipe or an antimicrobial hand sanitizer composition.

In another aspect of the present invention, the composition of the present invention is suitable for use in wipes for personal hygiene.

The present invention also relates to a method of inhibiting the growth of *Malassezia furfur* comprising the step of applying a composition of the first aspect on to the scalp of an individual. Alternately and preferably the above step is followed by rinsing the surface with water. The step of rinsing is generally carried out within 1 to 5 minutes after application of the composition on the skin or hair/scalp. According to one aspect, the invention provides for non-therapeutic benefits.

The method is more effective when the mole ratio of the polyvalent metal salt of pyrithione to the piperazine compound on the *Malassezia furfur* cell is in the range of 1:80 to 1:5000.

The invention will now be illustrated with reference to the following non-limiting examples.

EXAMPLES

The synergistic interaction between the ZPTO and the piperazine compounds was determined using the ΣFIC assay. A brief description of the method is given below.

Methods: ΣFIC Assay Against *Malassezia furfur*

Microorganism Preparation:

*M. furfur* (CBS 1878) was maintained on MD agar plate (Solution A) was cultured into 20 ml of growth medium Pityrosporum Broth (PB, Solution B).

Solution A Preparation

| Modified Dixon Agar (MD) | |
|---|---|
| 36 g | Malt Extract (Oxoid) |
| 6 g | Mycological Peptone (Oxoid) |
| 10 | Purified Agar (Oxoid) |
| 20 g | Ox-bile (Oxoid) |
| 2 ml | Oleic acid (Sigma) |
| 2 ml | Glycerol (Sigma) |
| 10 ml | Tween 40 (Sigma) |
| Deionized Water to 1000 ml | |
| 50 mg (1 vial) dissolved in 2 ml 95% ethanol | |
| Chloramphenicol (Oxoid SR078E) | |
| (Ensure stirring thoroughly including after autoclaving) | |

Solution B Preparation

| Pityrosporum Broth (PB) | |
|---|---|
| 10 g | Bacteriological Peptone |
| 0.1 g | Yeast extract |
| 10 g | Ox-bile |
| 2.5 g | Taurocholic acid |
| 10 g | Glucose |
| 1 L | Deionised water |
| 0.5 ml | Tween60 |
| 1 ml | Glycerol |
| Adjust pH to 6.2 | |
| After sterilization | |
| 0.5 ml | UHT milk |

They are then incubated at 32° C. for 48 hrs with shaking. Then, 1 ml of the first broth culture is transferred into 9 ml of fresh PB and incubated at 32° C. for 48 hrs with shaking. The final culture should contain 2 to $6 \times 10^6$ cells/ml. This is achieved by diluting using PB to $5*10^6$ cell/ml.

In-Vitro Susceptibility Testing

Zinc pyrithione was serially diluted (2-fold) to prepare in a range of 2-125 ppm in the growth medium. The piperazine compound was serially diluted (2-fold) to prepare in a range of 10-10,000 ppm in growth medium.

Binary combinations of ZPTO and the testing compound were prepared in 96-well plate by mixing 20 μl of zinc pyrithione solution with 20 μl of testing compound. The solution in each well were further mixed with 160 μl of PB and 20 μl of M. furfur. The final cell density in the testing plate is around $5*10^4$ cell/ml, and the final concentration of actives in each well of the 96-well plate were shown below.

ZPTO concentrations (in ppm): 12.5, 6.3, 3.1, 1.6, 0.8, 0.4, 0.2 and 0

Piperazine compound concentrations (in ppm): 1000, 500, 250, 125, 62.5, 31.3, 15.6, 7.8, 3.9, 2.0, 1.0 and 0.

The plate was incubated at 32° C. for one day. Then 20 μl of alamar blue (0.01%) was added into each well with a further incubation for one day to observe the color change. Red color indicates microbial growth and the non-changing blue color indicates no growth. In addition, it was also confirmed that the testing compound alone will not cause color change of alamar blue with a control mixture without adding microbes.

Calculation:

(1) Minimum Inhibition Concentration (MIC):

The MIC is defined as the absolute lowest concentration of active that provides complete microbial growth inhibition as indicated by the blue color of alamar blue under the tested condition. For example, for zinc pyrithione, the MIC was determined to be 1.6-3.2 ppm.

The MIC of 1-(2-fluorobenzoyl)-4-(4-phenyl cylcohexyl) piperazine was determined to 100 ppm. 1-(3-chlorobenzyl)-4-(4-ethylbenzyl)piperazine oxalate, 1-(4-fluorophenyl)-4-isobutyrylpiperazine, and 1-isobutyryl-4-phenylpiperazine were determined to be higher than 1000 ppm. The MIC of 1-(4-ethylbenzyl)-4-(4-methylcyclohexyl)piperazine oxalate was determined to be 125 ppm.

(2) Fractional Inhibition Concentration (FIC):

The differing behaviours of inhibitory antimicrobials in isolation and mixtures have been widely explored using the concept of the Fractional Concentration (FC) and Fractional Inhibitory Concentration (FIC). The parameter can be defined as follows:

$$FIC\ (component\ a) = \frac{MIC\ (component\ a\ tested\ in\ the\ mixture)}{MIC\ (component\ a\ tested\ as\ a\ single\ active)}$$

(3) Synergy and Additivity

The interactions between antimicrobials can be additive, synergistic or antagonistic depending on whether the efficacy of the combination is equivalent to, greater than or less than that obtained for the same total concentration of the individual components when tested alone.

These relationships can be expressed mathematically by summing the fractional MIC values for all the components present in the mixture to give the "fractional inhibition index". There is no consistent approach in the academic or patent literature in defining precise limiting ΣFIC values that differentiate synergy from additivity or antagonism. In this study, we have adopted a liberal approach defining any binary mixture with ΣFIC<0.9 as showing evidence of synergistic behavior.

ΣFIC=FIC (component 1)+FIC (component 2)

ΣFIC=1 corresponds to additive bactericidal activity

ΣFIC>1 corresponds to antagonistic bactericidal activity

ΣFIC<0.9 corresponds to synergistic bactericidal activity

4. Results:

Based on the concentration range of ZPTO (0 to 12.5 ppm) and the piperazine compound (0 to 1000 ppm) at which the experiments were carried out, the ΣFIC of the combinations is given below.

| Example | Combination | ΣFIC |
|---|---|---|
| 1 | ZPTO + 1-(2-fluorobenzoyl)-4-(4-phenyl cylcohexyl) piperazine | 0.25 |
| 2 | ZPTO + 1-(3-chlorobenzyl)-4-(4-ethylbenzyl)piperazine oxalate | 0.63 |
| 3 | ZPTO + 1-(4-fluorophenyl)-4-isobutyrylpiperazine | 0.75 |
| 4 | ZPTO + 1-isobutyryl-4-phenylpiperazine | 0.75 |
| 5 | ZPTO + 1-(4-ethylbenzyl)-4-(4-methylcyclohexyl)piperazine oxalate | 0.75 |

The data in Table above indicates that both the piperazine compounds in combination with ZPTO exhibit synergistic antimicrobial activity.

The invention claimed is:

1. A synergistic antimicrobial composition comprising:
   a polyvalent metal salt of pyrithione; and
   a piperazine compound selected from 1-(2-fluorobenzoyl)-4-(4-phenyl cyclohexyl)piperazine, 1-(3-chlorobenzyl)-4-(4-ethylbenzyl)piperazine oxalate, 1-(4-fluorophenyl)-4-isobutyrylpiperazine, 1-isobutyryl-4-phenylpiperazine, or 1-(4-ethylbenzyl)-4-(4-methylcyclohexyl)piperazine oxalate.

2. The composition as claimed in claim 1, wherein the polyvalent metal salt of pyrithione is zinc pyrithione.

3. The composition as claimed in claim 1, wherein the composition comprises 0.1 to 5.0% of the polyvalent metal salt of pyrithione by weight of the composition.

4. The composition as claimed in claim 1, wherein the composition comprises 0.1 to 10% piperazine compound by weight of the composition.

5. The composition as claimed in claim 1, wherein the piperazine compound is 1-(2-fluorobenzoyl)-4-(4-phenyl cyclohexyl)piperazine or 1-(3-chlorobenzyl)-4-(4-ethylbenzyl) piperazine oxalate.

6. The composition as claimed in claim 1, wherein the composition comprises a cosmetically acceptable carrier comprising water.

7. The composition as claimed in claim 6, wherein the carrier further comprises a surfactant.

8. The composition as claimed in claim 1, wherein the composition is a wash-off or leave-on hair care composition.

9. The composition as claimed in claim 8, which is a shampoo or a hair conditioning composition.

10. A method of inhibiting the growth of Malassezia furfur comprising:
    topically applying a synergistic antimicrobial composition to the skin, hair, or scalp of an individual,
    wherein the synergistic antimicrobial composition comprises:
    a polyvalent metal salt of pyrithione; and
    a piperazine compound selected from 1-(2-fluorobenzoyl)-4-(4-phenyl cyclohexyl)piperazine, 1-(3-chlorobenzyl)-4-(4-ethylbenzyl)piperazine oxalate, 1-(4-fluorophenyl)-4-isobutyrylpiperazine, 1-isobutyryl-4-phenylpiperazine, or 1-(4-ethylbenzyl)-4-(4-methylcyclohexyl)piperazine oxalate.

11. The method as claimed in claim 10, wherein the method further comprises rinsing the skin, hair, or scalp of the individual with water.

12. The method as claimed in claim 10, wherein the polyvalent metal salt of pyrithione is zinc pyrithione.

13. The method as claimed in claim 10, wherein the antimicrobial composition comprises 0.1 to 5.0% polyvalent metal salt of pyrithione by weight of the antimicrobial composition.

14. The method as claimed in claim 10, wherein the antimicrobial composition comprises 0.1 to 10% piperazine compound by weight of the composition.

15. The method as claimed in claim 10, wherein the piperazine compound is 1-(2-fluorobenzoyl)-4-(4-phenyl cyclohexyl)piperazine or 1-(3-chlorobenzyl)-4-(4-ethylbenzyl) piperazine oxalate.

* * * * *